(12) United States Patent
Knutson

(10) Patent No.: US 8,287,275 B2
(45) Date of Patent: Oct. 16, 2012

(54) OCCLUSAL INDICATOR TRAY AND PROCESSES THEREFOR

(76) Inventor: Eric Jon Knutson, Granite Bay, CA (US)

( * ) Notice: Subject to any disclaimer, the term of this patent is extended or adjusted under 35 U.S.C. 154(b) by 951 days.

(21) Appl. No.: 11/207,623

(22) Filed: Aug. 11, 2005

(65) Prior Publication Data

US 2007/0037116 A1   Feb. 15, 2007

(51) Int. Cl.
*A61C 9/00* (2006.01)
(52) U.S. Cl. .......................................................... 433/37
(58) Field of Classification Search .................... 433/68, 433/37, 215, 6, 48, 214, 41, 42, 34, 71; 264/16–18
See application file for complete search history.

(56) References Cited

U.S. PATENT DOCUMENTS

| 4,531,914 A * | 7/1985 | Spinello ........................ 433/136 |
| 4,553,936 A * | 11/1985 | Wang ............................... 433/37 |
| 5,011,407 A * | 4/1991 | Pelerin ............................. 433/48 |
| 2003/0224319 A1* | 12/2003 | Liddle .............................. 433/38 |
| 2006/0269904 A1* | 11/2006 | Suchan et al. ................. 433/213 |

* cited by examiner

*Primary Examiner* — Sunil K Singh

(57) ABSTRACT

A mouthpiece for forming custom dental trays intraorally having a sheet of low-melting custom tray material sealingly containing a moldable filler. The mouthpiece may also have flexible walls along the facial-buccal or lingual sides for additional support. The mouthpiece can form custom trays for both arches simultaneously, or for a single arch. In typical use, the mouthpiece is heated, opposing arches of teeth forcefully bite into the tray material and contained filler, thereby molding the tray material to fit the teeth, the tray material is cooled, the mouthpiece is removed from the teeth, and excess tray material is trimmed away to form trays for both arches.

2 Claims, 12 Drawing Sheets

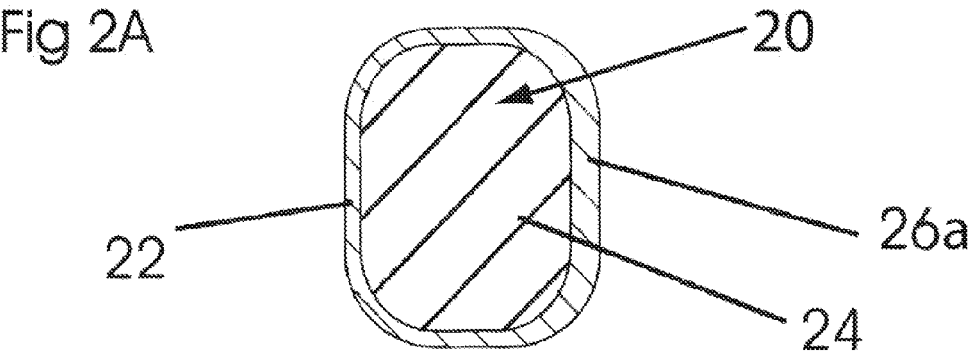
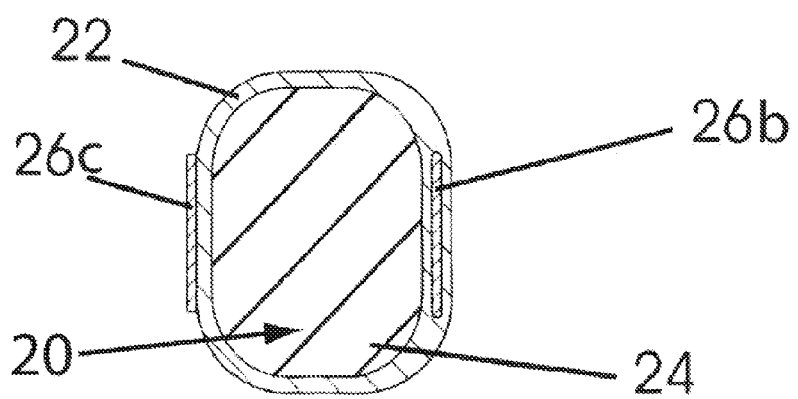
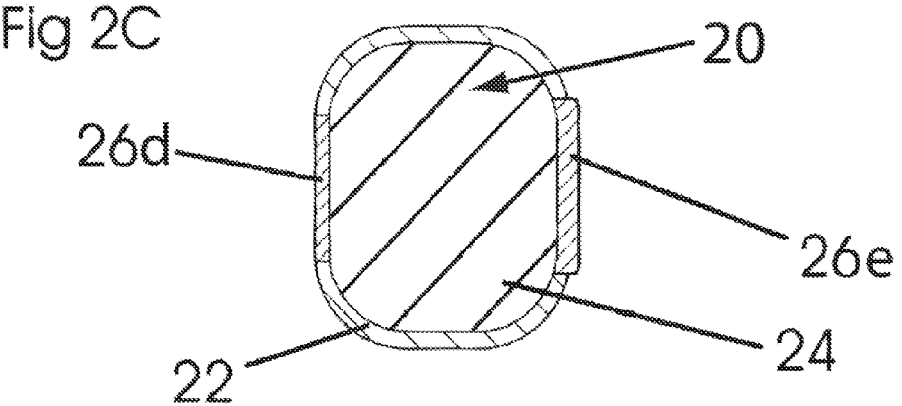

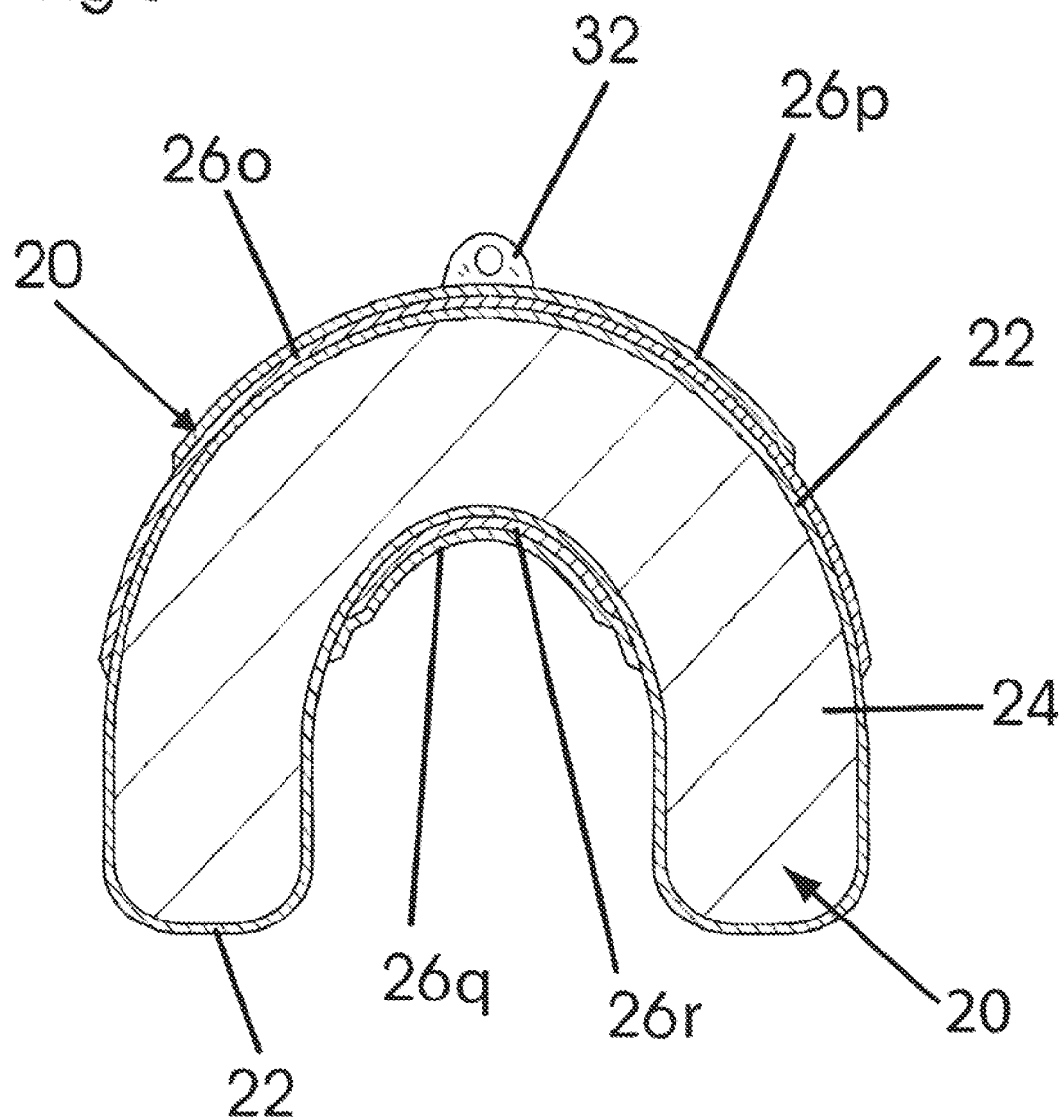

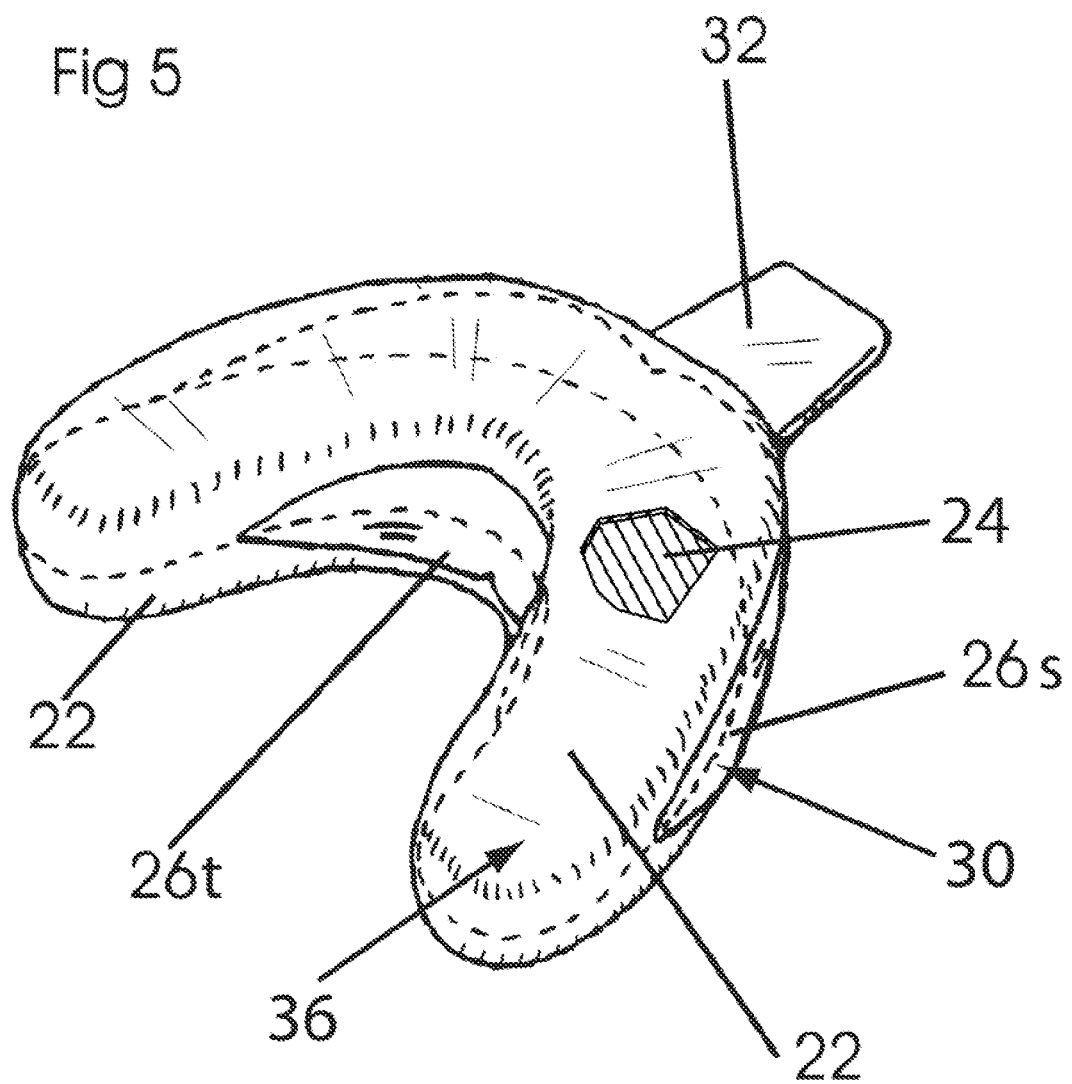

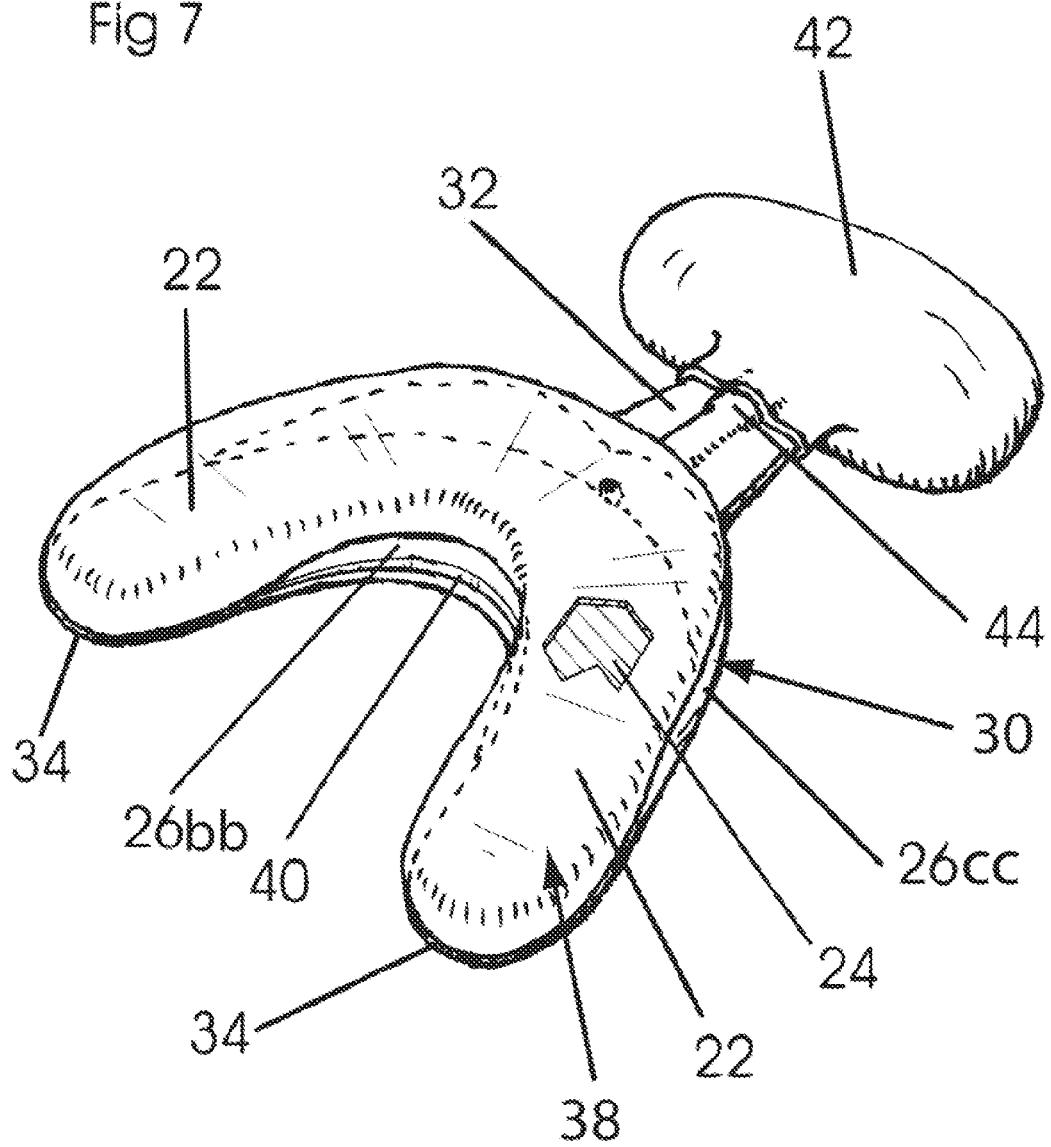

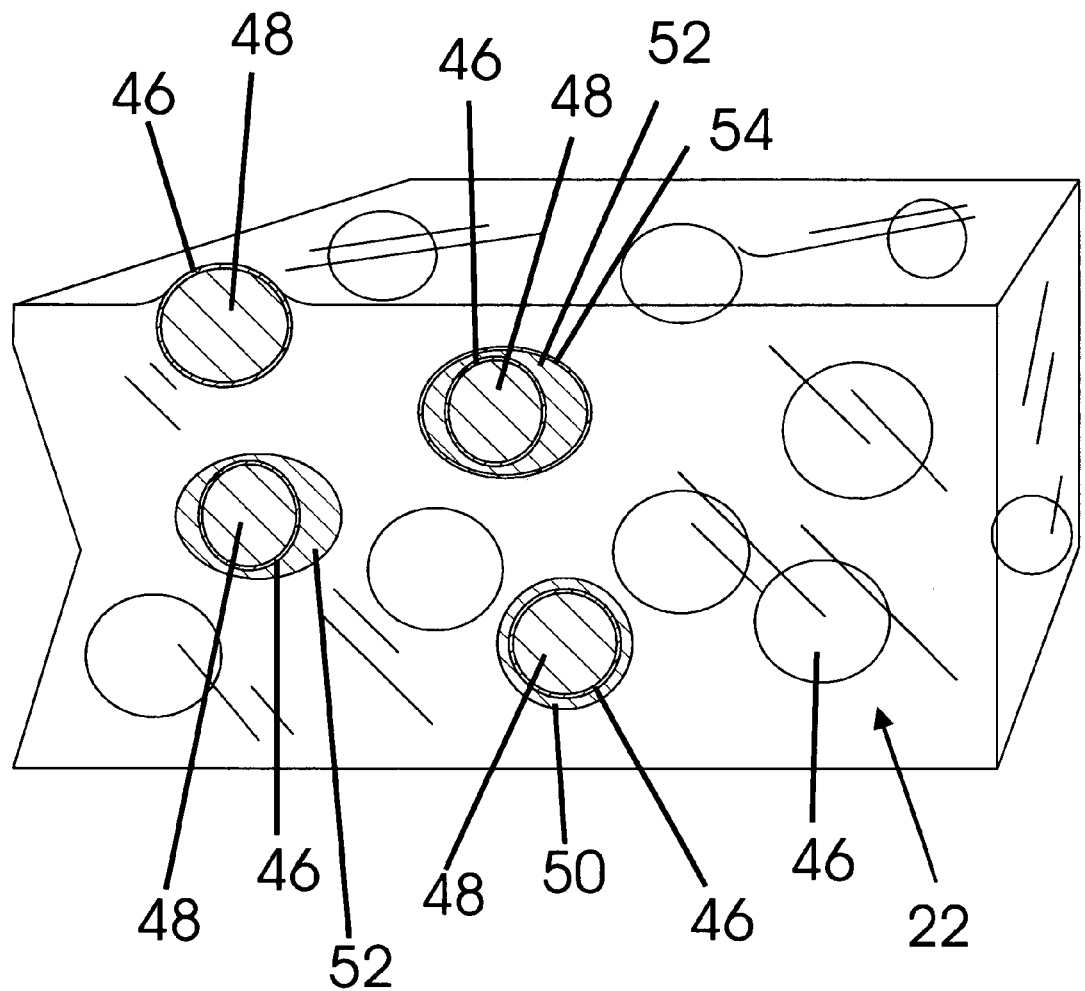

OCCLUSAL INDICATOR TRAY AND PROCESSES THEREFOR

BACKGROUND

1. Field of Invention

This invention relates to custom dental trays, specifically to custom dental trays that indicate pressure from occlusal contact.

2. Occlusal Treatment

Splints, stents, and night guards are types of dental appliances which have been fitted with sensors to indicate pressure from occlusal contact. Generally, such appliances are fairly costly and time consuming to fabricate, and are made by a dental laboratory. They are useful for collecting data on dental occlusion, jaw muscle activity during sleep, and so on. Such appliances are primarily used to diagnose or treat patients exhibiting high levels of activity in the muscles of mastication during various stages of sleep, known as bruxism, or mandibular parafunction. Patients generally take such appliances to their homes, and wear them in the mouth during sleep, typically accompanied by one or more data collection or analysis devices. Generally, patients who receive treatment with these appliances are symptomatic, and are well aware that they have an advanced problem that needs treatment.

In contrast, there is a large group of people who are unaware that they have a problem that needs treatment. Many people exhibit moderate levels of parafunction, but do not have sufficient symptoms to cause them to believe they need treatment. They are predominantly unaware that they are slowly chipping or wearing away their teeth, slowly spreading fractures through their teeth, weakening exisiting dental restorations, traumatizing the alveolar bone around the teeth, traumatizing their temporomandibular joints, or causing pain in the head or neck. They tend to become aware of these problems only when they have unnecessarily progressed to obvious symptoms, have lost function or structure, and need more costly treatment.

Sleep research shows that approximately one third of the general population could benefit from use of a simple hard night guard. Generally, hard night guards are made by a dental laboratory, are time consuming to fabricate, require multiple office visits to fit, and are somewhat costly for patients. Therefore, patients must somehow become aware that they could benefit from the use of a night guard before they will want to proceed with night guard fabrication.

Dental practitioners are able to rapidly assess signs of parafunction, such as linea alba, serrated tongue, TMJ irregularities, dental attrition, vertical bone loss, and so on. However, even if time is taken to show patients these signs, they remain relatively meaningless to them. A practitioner can spend significant time describing the sequelae of these problems to patients, but patients are generally not motivated to treat problems that they see little or no direct evidence of. Dental practitioners therefore have the undesirable task of being obligated to inform patients that they need a somewhat costly night guard to prevent a problem the patient is not sure they have. Therefore, dental practitioners need of a rapid, low cost means to help patients realize that significant parafunction is indeed occurring.

In addition, indicators of occlusion are useful in the practice of dentistry for a variety of other purposes, including occlusal studies, occlusal records, prosthetic fitting, and so on.

3. Description of Prior Art

Custom trays are trays which are designed to custom fit over at least a portion of a person's teeth. Custom trays generally fit with a greater accuracy of adaptation to the shapes of the teeth than stock trays. Custom trays are used in dentistry for performing various functions in the mouth. These functions include impression material carrier, bruxism protection, athletic guard, airway maintenance, surgical stents, medicament carrier, and so on. Medicaments to be carried in custom trays include tooth whitening agents, anti-cariogenic agents, antibacterial agents, desensitizing agents, and so on. In contrast to the laboratory fabricated splints, stents and night guards with occlusal pressure indicators, custom trays are commonly made in dental offices.

In one common process for forming custom dental trays, the steps include taking impressions of the teeth, pouring plaster into the impressions to form plaster models of the teeth, providing a manufactured square-cut or round-cut thin sheet of a custom tray sheet having a specified uniform thickness, heating said sheet until it is moldable, applying a specialized vacuum source to the moldable sheet to mold it to fit the shapes of the teeth on the plaster model, allowing the moldable sheet to cool until it becomes a non-moldable sheet, and trimming the non-moldable sheet to form a dental tray. Trays formed with this process tend to be accurately conformed to the teeth, have good retention to the teeth, and have a low rate of fluid leakage.

Due to the moderate cost of the specialized vacuum source used in the above process, and the skill of the personnel required, this method of forming custom trays is performed in dental offices or dental laboratories. In addition, while forming custom trays using this process can be accomplished in a single patient visit, it is much more common for an additional patient visit to be made to deliver the completed trays, due to the amount of time required to complete the trays.

In a second process for forming custom dental trays, a low melting point polymer tray material is heated until moldable, and then molded intraorally to conform it to fit the shapes of the teeth. The process for molding the tray material intraorally include instructing the patient to bite down lightly, push the tongue against the roof of the mouth, suck air and water out of their mouth, conform the tray material to the shapes of the teeth with fingers, then remove and hold under cold water. The custom tray material and process is intended to reduce the time required to form a custom dental tray. It is also intended to permit the formation of a custom dental tray without the need for costly specialized vacuum equipment, or skilled dental office personnel. Such custom dental trays could be constructed rapidly by dental office personnel, or could be constructed by unskilled persons at home. However, trays made with this process tend to be less accurately conformed to the teeth.

In a third process for forming custom dental trays, there is provided a thin pliable inner sheet of tray material nested in an outer thicker dental tray. The pliable inner tray is pre-loaded with a medicament, such as a sticky whitening gel. The thicker tray is used to seat the pliable inner tray on the dental arch, and is then discarded. The pliable inner tray is adhered to the teeth via the sticky medicament, and is finger-molded to enhance adaptation to the teeth. The moldability of the pliable inner tray material is not substantially altered during this process. Trays made with this process tend to be less accurately conformed to the teeth.

In a fourth process for forming custom dental trays, a pliable tray is pre-loaded with a sticky medicament. The pliable tray is adhered to the teeth via the sticky medicament, and is finger molded to enhance adaptation to the teeth. The moldability of the pliable tray material is not substantially altered during this process. Trays made with this process tend to be less accurately conformed to the teeth.

In a fifth process for forming custom dental trays, a dental impression is made of the teeth. The teeth are forcefully pushed into the cured impression imprint with a sheet of moldable tray material interposed, thereby molding the tray material to the shapes of the teeth to the form a custom tray. Trays made with this process tend to be conformed to the teeth with moderate accuracy.

In a sixth process for forming custom dental trays, an imprint is made of the teeth in a dense putty. The teeth are forcefully pushed into the uncured imprint with a sheet of moldable tray material interposed, thereby molding the tray material to the shapes of the teeth to the form a custom tray. Trays made with this process tend to be conformed to the teeth with moderate accuracy.

The above processes for forming custom dental trays suffer from a number of disadvantages:

(a) Accurately adapted trays require skilled personnel
(b) Accurately adapted trays require costly specialized equipment
(c) Accurately adapted trays can require substantial time
(d) Trays formed are not capable of indicating occlusal pressure
(e) Trays formed intraorally tend to have moderate to poor adaptation to the teeth
(f) Trays formed intraorally tend to have moderate to poor retention to the teeth
(g) Trays formed intraorally tend to have substantial fluid leakage A tray material and process similar to my custom dental tray material and process would not have been as practical prior to the development of low melting polymers, or other materials which are moldable at temperatures which are tolerated intraorally, and then can be caused to become substantially non-moldable.

BRIEF DESCRIPTION OF THE INVENTION

The present invention is directed to fabricating custom dental trays quickly and inexpensively, such as by molding custom dental trays intraorally, and especially to forming custom trays which can indicate occlusal contact pressure. Custom trays which can indicate occlusal contact pressure may be useful for the detection, evaluation, and treatment of occlusion, mandibular parafunction, myofacial pain, and so on. However, custom trays may also be useful for retaining medicaments, as a night guard, for retaining attachments in the mouth, such as a false tooth, and so on.

The invention provides a mouthpiece for forming custom dental trays. In a first embodiment, the mouthpiece is arch-shaped and comprised of a moldable sheet, such as a sheet of custom tray material, which contains a moldable filler, such as air.

It is preferred that said moldable sheet is comprised a low melting material, having a melting range between 40° to 85° C., such that said sheet may be placed into the mouth after heating to the melting range without burning the oral tissues.

It is preferred that a pressure indicating means is embedded in said sheet, for indicating occlusal pressures exerted on a custom tray formed from said sheet.

In a second embodiment, a double-arch mouthpiece, a thin, flexible connector extends from the buccal-facial side of said mouthpiece to the lingual side of said mouthpiece to provide a degree of support for a moldable sheet. Said moldable sheet and a contained moldable filler are present on either side of said connector. It is preferred that flexible facial and lingual walls further provide support for said moldable sheet, and that a handle extends mesially from said facial wall.

In a third embodiment, a single-arch mouthpiece, a connector extends from the buccal-facial side of said mouthpiece to the lingual side of said mouthpiece to provide a degree of support for a moldable sheet. Said moldable sheet and a contained moldable filler are present on only one side of said connector. It is preferred that flexible facial and lingual walls further provide support for said moldable sheet, and that a handle extends mesially from said facial wall.

In a typical process for said mouthpieces, said sheet is caused to be moldable, such as by heating. A mouthpiece is placed into a person's mouth, and the teeth are forcefully seated into said sheet. Said contained filler provides sufficient resistance pressure against the forceful seating to mold said sheet to fit the shapes of the teeth.

OBJECTS AND ADVANTAGES

Accordingly, several objects and advantages of my invention and process are to facilitate the formation of accurately adapted custom dental trays:

(a) by persons unskilled in the art without the use of costly equipment
(b) in fewer steps, and requiring less time, than other processes
(c) for maxillary and mandibular arches simultaneously
(d) which have low fluid leakage and substantial retention
(e) which can indicate occlusal contact pressure
(f) by persons unskilled in the art in order to retain attachments Further objects and advantages are to provide a custom dental tray which can by made by persons of the general public. Still further objects and advantages will become apparent from a consideration of the ensuing description and drawings.

DRAWING FIGURES

In the drawings, closely related figures have the same number, but different alphabetic suffixes.

FIGS. 2A-2E shows cross-sectional views of a basic mouthpiece comprised of a moldable sheet, a contained moldable filler, and supporting walls in various configurations.

FIG. 3 shows a cross-sectional top view of a basic mouthpiece comprised of a moldable sheet, a contained moldable filler, and supporting walls in various configurations.

FIG. 5 shows a perspective view of a double-arch mouthpiece having a frame that is supporting both maxillary and mandibular moldable sheets and contained moldable filler. A cutaway shows said filler.

FIG. 7 shows a perspective view of a single-arch mouthpiece having a frame that is supporting a single moldable sheet and a contained moldable filler, where said filler is shown in a cutaway.

FIG. 9 is an enlarged perspective cutaway view showing a moldable sheet having a multiplicity of capsules, wherein said capsules contain an indicator.

REFERENCE NUMERALS IN DRAWINGS

| 20 | basic mouthpiece | 22 | sheet |
|----|------------------|----|-------|
| 24 | filler | 26 | wall |
| 28 | separator | 30 | frame |
| 32 | handle | 34 | connector |
| 36 | double-arch mouthpiece | 38 | single-arch mouthpiece |
| 40 | element | 42 | source |
| 44 | valve | 46 | capsule |
| 48 | indicator | 50 | absorbant |
| 52 | space | 54 | container |
| 56 | tray | 58 | record |

DETAILED DESCRIPTION—FIGS. 1 TO 10

Figure 1:
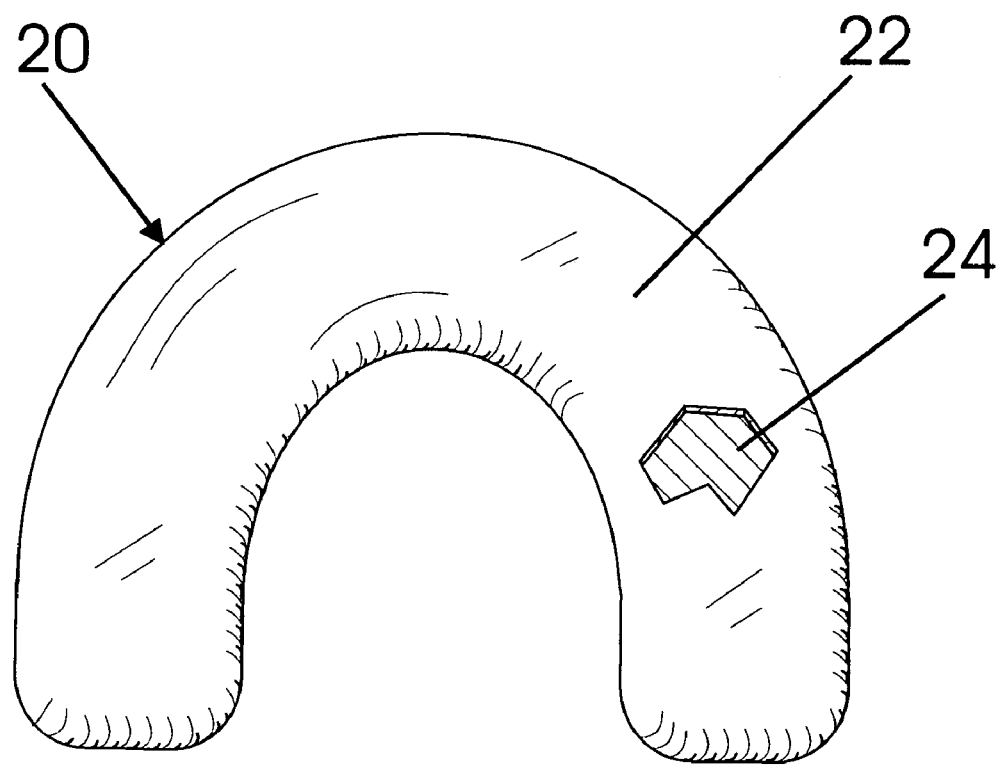
FIG. 1 shows a perspective view of a basic mouthpiece comprised of a moldable sheet and a contained moldable filler, where said filler is shown in a cutaway.

According to another aspect of the invention, there is provided an embodiment of a mouthpiece, basic mouthpiece 20, for use in the process of the invention, a typical embodiment of which is shown in perspective view in FIG. 1. Basic mouthpiece 20 is comprised of a moldable sheet, sheet 22, and a moldable space occupying material, filler 24, shown in a cutaway. Filler 24 sheet, sheet 22, and a moldable space occupying material, filler 24, shown in a cutaway. Filler 24 is sealed within, and entirely contained by, basic mouthpiece 20, and sheet 22 at least partly contains filler 24. Sheet 22 is comprised of a material that may be caused to be plastically deformable, or substantially moldable, and can subsequently be caused to be substantially non-moldable. Filler 24 provides sufficient resistance pressure to mold sheet 22 to fit the shapes of the teeth when the teeth are forcefully seated into sheet 22.

It is preferred that sheet 22 is comprised of custom dental tray material. It is further preferred that sheet 22 is a low melting material having a melting range between 40° and 85° C., such that sheet 22 will not burn oral tissues when heated to the melting range. Suitable materials include those containing ethylene vinyl acetate, ultra low density polyethylene, polycaprolactone, polyethylene, polypropylene, and so on. It is preferred that sheet 22 is comprised of a material that can be caused to be substantially moldable by the user during process of the present invention. However, sheet 22 may be provided substantially moldable by the manufacturer.

It is preferred that the surface of sheet 22 is non-textured. However, the surface of sheet 22 may be textured, such as to improve retention of an oral medicament, to influence the rate of delivery of an oral medicament, to influence light absorption, and so on.

It is preferred that sheet 22 is colorless and transparent. However, sheet 22 may be translucent or opaque, and sheet 22 may be tinted, such as tinted blue, so that sheet 22 may function as a light filter. A light-filtering sheet 22 may be useful to permit the passage of higher energy light wavelengths through sheet 22, while reflecting infrared wavelengths, and thereby facilitate the use of light-activated medicaments.

It is preferred that filler 24 is comprised of a gas, such as air or nitrogen. However, filler 24 may be comprised of water, other liquids, saline, flowable foam, elastic foam, non-elastic foam, gel, putty, clay, wax, silicone, elastomer, thermoplastic, light-curable or chemical curable materials, light-transmitting materials, and so on.

It is preferred that filler 24 is comprised of a material having a low heat capacity, so as to minimize user discomfort during molding of a heated sheet 22. However, filler 24 may be comprised of a higher heat capacity material, such as to facilitate molding of sheet 22.

If is preferred that filler 24 is sealingly contained in such a way that it is somewhat pressurized. However, filler 24 may be non-pressurized.

It is preferred that filler 24 remain moldable after sheet 22 has been molded to fit the shapes of the teeth. However, filler 24 may be caused to be non-moldable after sheet 22 becomes molded to fit the shapes of the teeth.

It is preferred that filler 24 is comprised of a homogeneous material. However, filler 24 may be comprised of non-homogenous materials. For a first example, portions of filler 24 in the central areas of basic mouthpiece 20 may have different physical properties than portions of filler 24 near the lingual or near the facial or buccal, hereinafter called the facial, of basic mouthpiece 20, such as higher durometer. For a second example, portions of filler 24 may be comprised of a separator material, such that contacting inner surfaces of moldable sheet 22 will be inhibited from adhering together. For a third example, filler 24 may be comprised of two different materials, such as air and water. For a fourth example, filler 24 may be comprised of two different materials, such as a pliable container containing a moldable material, wherein said pliable container is interposed between sheet 22 and said moldable material.

It is preferred that a small amount of sterile water, or water vapor, is contained with filler 24, such that said water may be heated by microwaving, and thereby facilitating heating sheet 22 to cause sheet 22 to be moldable.

It is preferred that basic mouthpiece 20 is configured so as to be useable primarily without a supporting stock dental tray. However, basic mouthpiece 20 is may be configured so as to be useable primarily with a supporting stock dental tray, such as by precontouring portions 22 that will be adjacent to said stock dental tray.

FIGS. 2A-2E show cross-sectional views of basic mouthpiece 20. There are other possible configurations which are not shown.

FIG. 2A shows a basic mouthpiece 20 where sheet 22 entirely contains filler 24. The facial portion of sheet 22 is thickened to form a wall, wall 26a. Wall 26a provides at least partial rigidity and resistance to deformation of basic mouthpiece 20.

FIG. 2B shows a basic mouthpiece 20 having a facial wall 26b embedded within sheet 22, and a lingual wall 26c located on the outer surface of sheet 22.

It is preferred that wall 26b and wall 26c are comprised of a material having different properties than sheet 22, such as different dimensions, durometer, melt points, translucency, pigment, and so on. However, wall 26b and wall 26c may be comprised of a material having the same properties as sheet 22, or is identical to sheet 22. It is further preferred that wall 26b in a given mouthpiece have different physical properties than wall 26c, or a third wall, and so on. However, multiple walls present in a mouthpiece may have similar physical properties, or be comprised of identical materials.

It is preferred that a separating material, separator 28, is interposed between the superior portion of sheet 22 and the inferior portion of sheet 22, so as to inhibit adhesion thereof, such as when a person's teeth are forcefully seated into moldable sheet 22, thereby causing formerly separated portions of sheet 22 to be in contact.

FIG. 2C shows a basic mouthpiece 20 having walls 26d and 26e located along the facial and lingual aspects of basic mouthpiece 20 respectively. Both the maxillary and the mandibular sheets 22 are shown sealingly connected to the respective ends of facial wall 26d and lingual wall 26e. As such, sheet 22 does not overlap walls 26d or 26e. Facial wall 26d is shown thicker than lingual wall 26e.

Figure 2D:
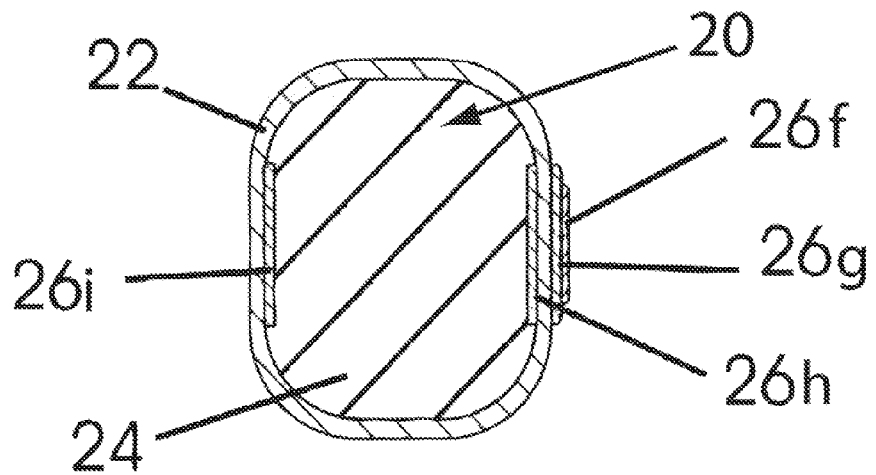

FIG. 2D shows a basic mouthpiece 20 having multiple facial walls 26f, 26h, and 26i, and lingual wall 26i, located on the inner and outer aspects of sheet 22.

Figure 2E:
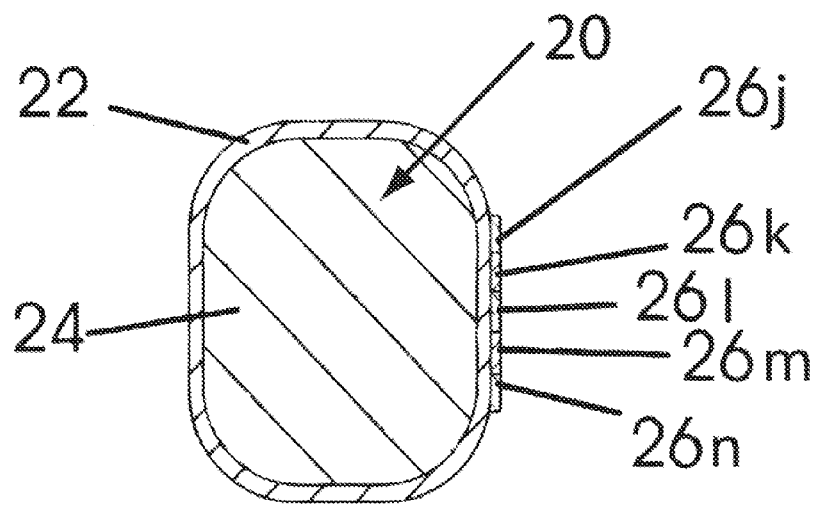

FIG. 2E shows a basic mouthpiece 20 having multiple walls, where five walls 26j, 26k, 26l, 26m, and 26n are located on the facial aspect of sheet 22, wherein individual walls 26 have unique physical properties, such as durometer.

FIG. 3 shows a top view of a basic mouthpiece 20 having multiple walls, where two walls 26o and 26p are layered on the facial aspect of sheet 22, and two walls 26q and 26r are layered on the lingual aspect of sheet 22.

Figure 4:
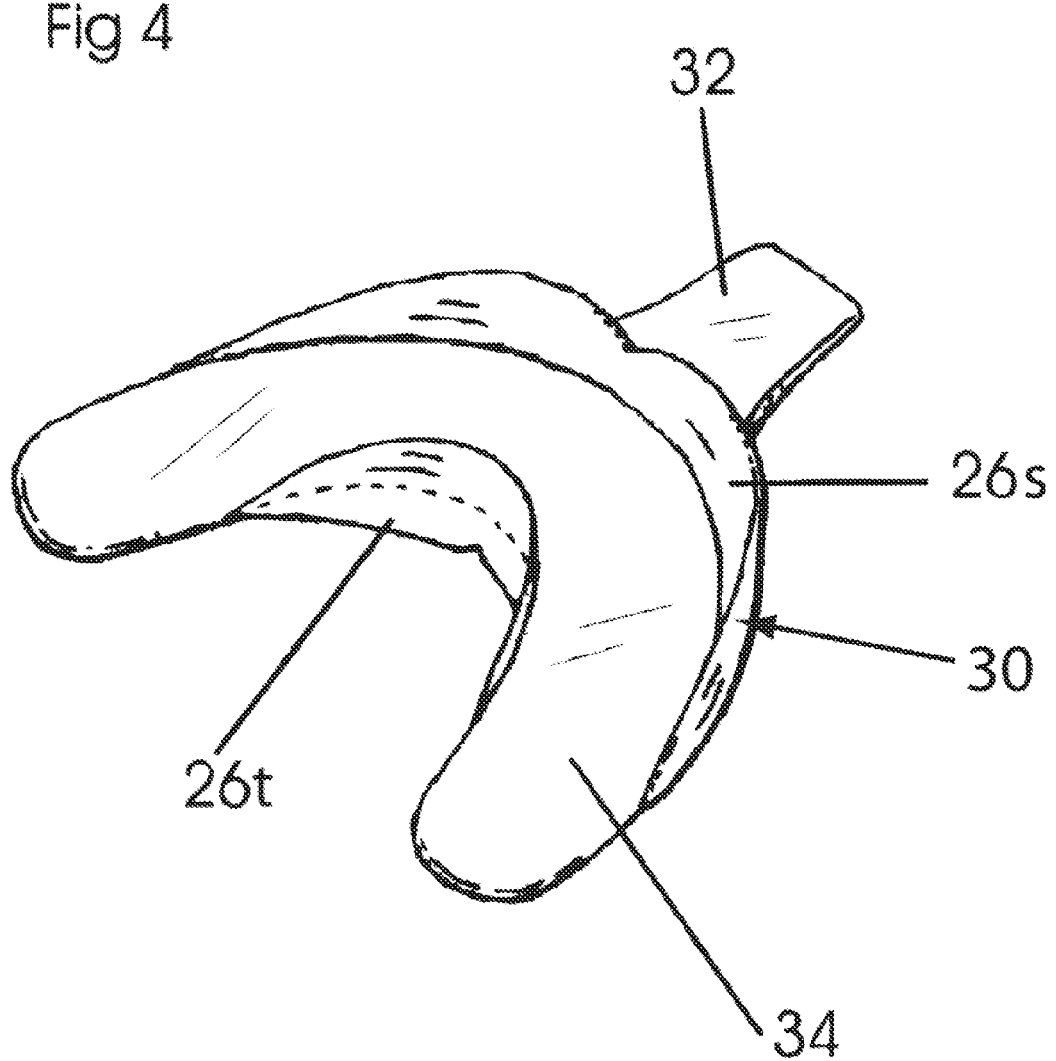
FIG. 4 shows a perspective view of a frame for supporting both maxillary and mandibular moldable sheets.

FIG. 4 shows a perspective view of a frame, frame 30, for supporting maxillary and mandibular moldable sheets. Frame 30 is comprised of a connector, connector 34, and at least one wall. Connector 34 is shown connecting a facial wall 26s to a lingual wall 26t. A handle, handle 32, is shown connected to facial wall 26s. It is preferred that handle 32 is rigid.

It is preferred that connector 34 is thin, so as to minimize interferences with occlusion of various dental arches. It is further preferred that connector 34 is flexible, such that a connected lingual wall 26t is able to move somewhat relative to a connected facial wall 26s, within the limitations of connector 34. However, connector 34 may be rigid, such as to provide support during forceful seating of a mouthpiece onto a dental arch, or to increase rigidity of walls 26s and 26t, and so on.

FIG. 5 shows a perspective view of an embodiment of a double-arch mouthpiece, double-arch mouthpiece 36, comprised of a frame 30 that is supporting maxillary and mandibular portions of sheets 22, hereinafter called maxillary sheet 22 and mandibular sheet 22, where sheet 22 at least partly contain filler 24. A cutaway shows filler 24. Also shown are facial wall 26s, lingual wall 26t, and handle 32.

FIG. 6A-6D show cross-sectional views of double-arch mouthpiece 36 with maxillary and mandibular sheets 22, where sheets 22 at least partly contain filler 24. There are other possible configurations which are not shown.

Figure 6A:
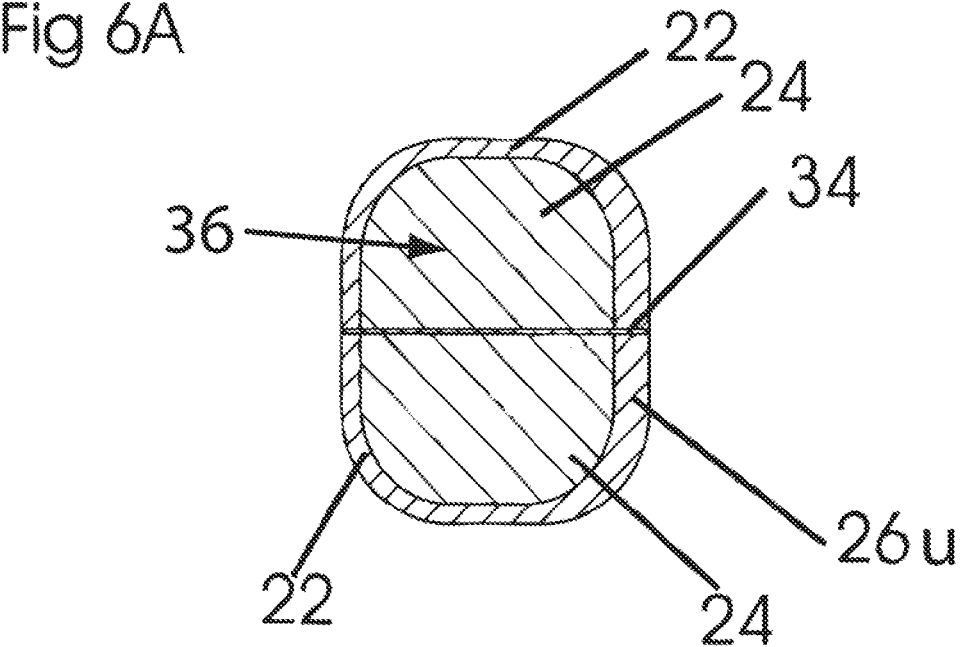
FIGS. 6A-6D shows cross-sectional views of various configurations of tray walls for supporting maxillary and mandibular moldable sheets and contained moldable filler.

FIG. 6A shows double-arch mouthpiece 36 with connector 34 connecting lingual sheet 22 to facial wall 26u, wherein facial wall 26u is comprised of a thickened sheet 22.

Figure 6B:
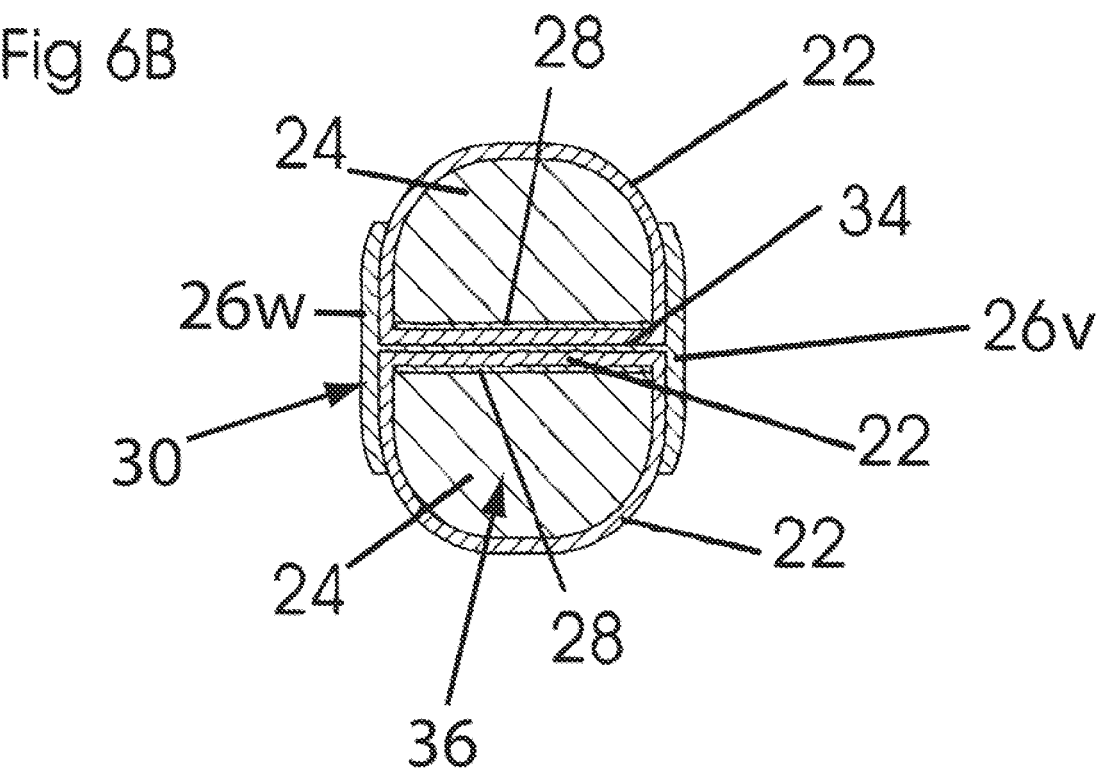

FIG. 6B shows double-arch mouthpiece 36, wherein frame 30 supports separate maxillary and mandibular sheets 22. Maxillary sheet 22 and mandibular sheet 22 each sealingly contain filler 24. Connector 34 connects facial wall 26v to lingual wall 26w. Separator 28 is shown lining the inner surface of maxillary and mandibular sheets 22.

It is preferred that both the maxillary and mandibular sheets 22 with contained filler 24 are removable from walls 26v and 26w and from connector 34. However, sheet 22 may be affixed to wall 26v, wall 26w, or connector 34.

Figure 6C:
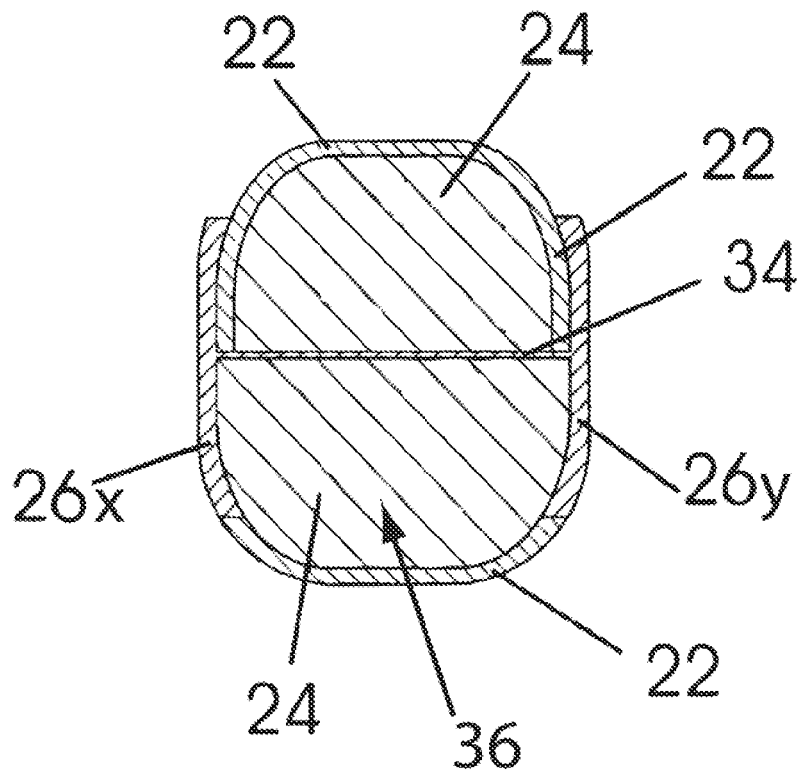

FIG. 6C shows double-arch mouthpiece 36 with connector 34 connecting a lingual wall 26x to a facial wall 26y, wherein walls 26x and 26y sealingly connect to a maxillary sheet 22 and a mandibular sheet 22. Maxillary sheet 22 extends from the facial end of connector 34 to the lingual end of connector 34, and along the inner surface of the maxillary portion of walls 26x and 26y. Mandibular sheet 22 extends from the inferior end of facial wall 26y to the inferior end of lingual wall 26x.

Figure 6D:
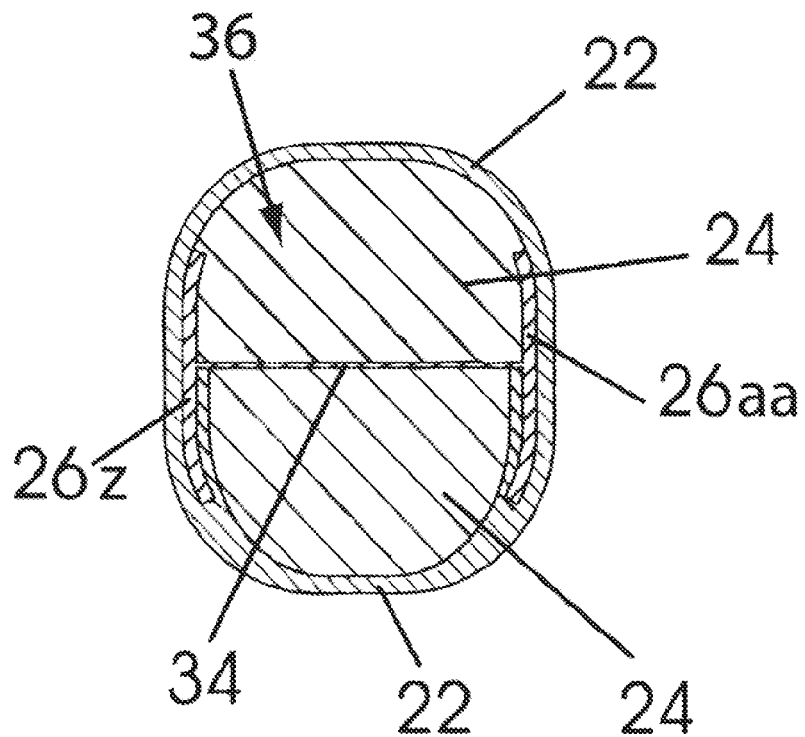

FIG. 6D shows double-arch mouthpiece 36 with connector 34 connecting a lingual wall 26z to a facial wall 26aa, wherein sheet 22 sealingly contains walls 26z and 26aa, connector 34, and filler 24. Maxillary walls 26z and 26aa are shown located along the inner surface of sheet 22, and mandibular walls 26z and 26aa are shown embedded within sheet 22.

FIG. 7 shows a perspective view of an embodiment of a single-arch mouthpiece, single-arch mouthpiece 38, comprising a sheet 22, filler 24, and connector 34, wherein sheet 22 at least partly contains filler 24 on only one side of connector 34. A cutaway shows filler 24. Also shown are lingual wall 26bb and facial wall 26cc, and handle 32.

It is preferred that connector 34 of single-arch mouthpiece 38 is rigid, to provide support for sheet 22 and walls 26bb and 26cc, especially during forceful seating of the teeth into sheet 22. However, connector 34 may be thin and flexible.

It is preferred that sheet 22 is affixed to walls 26bb and 26cc or connector 34. However, sheet 22 may removable from single-arch mouthpiece 38, such as when sheet 22 entirely contains filler 24.

It is preferred that the overall configurations of single-arch mouthpiece 38, as well as basic mouthpiece 20 and double-arch mouthpiece 36, are alterable to be fitted to individual dental arches, such as to fit dental arches having larger or smaller arch curvatures. It is further preferred that a memory element, element 40, is associated with wall 26, or sheet 22, such that an altered mouthpiece arch curvature may be stabilized. It is preferred that element 40 is comprised of a ductile metal strip, such as soft stainless steel, copper or aluminum. However element 40 may be comprised of less ductile metals, haywire, a linked chain with stiff joints, a linked chain with ratcheting joints, thermoplastic vinyl, polycaprolactone, and so on. However, said mouthpieces may be alterable by other means, such as by comprising walls 26bb and 26cc, connector 34, or frame 30 of materials similar to materials comprising element 40, or the curvatures of said mouthpieces may be substantially unalterable.

An exposure source, source 42, is shown wherein sheet 22 may be caused to become non-moldable at an accelerated rate due to an exposure emanating from source 42. It is preferred that source 42 exposes sheet 22 to a coolant, such as by injecting a coolant into filler 24, thereby cooling the inner surface of sheet 22. Suitable coolants include water, air, 1,1,1,2-tetrafluoroethane, ethyl chloride, and so on. However, source 42 could expose sheet 22 or filler 24 to light, to cross-linking chemicals, and so on.

It is preferred that source 42 is a small, pressurized can of 1,1,1,2-tetrafluoroethane having a metered atomizer button, where the can is pre-attached to handle 32. However, source 42 may be an elastic hand-squeezable bulb as shown in FIG. 7, a dental air-water syringe, a syringe, a connection to tap water, a connection to a pressurized can of air, a connection to a pressurized can of cross-linker, a curing light, and so on. It is preferred that source 42 is provided for the user as part of a kit that user purchases, wherein said kit includes a mouthpiece, and other needed supplies.

It is preferred that mouthpieces 20, 36, and 38 have an exposure entry port, valve 44, for source 42. It is further preferred that valve 44 is a one-way valve, such as a valve that would permit injection of a substance into filler 24 without permitting filler 24 to leak out through valve 44. However, valve 44 may be a light fiber-bundle, an ampoule stopper, and so on.

It is preferred that valve 44 is associated with handle 32. However, valve 44 may be located on a wall 26, or on sheet 22, and so on.

Figure 8A:
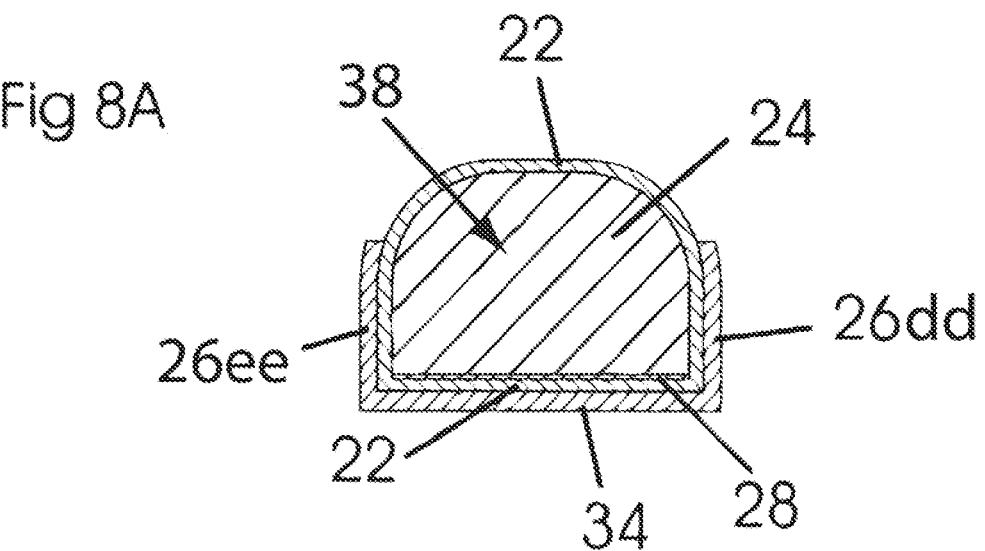
FIGS. 8A-8C shows cross-sectional views of various configurations of frame walls supporting a single-arch moldable sheet and a contained moldable filler.
Figure 8B:
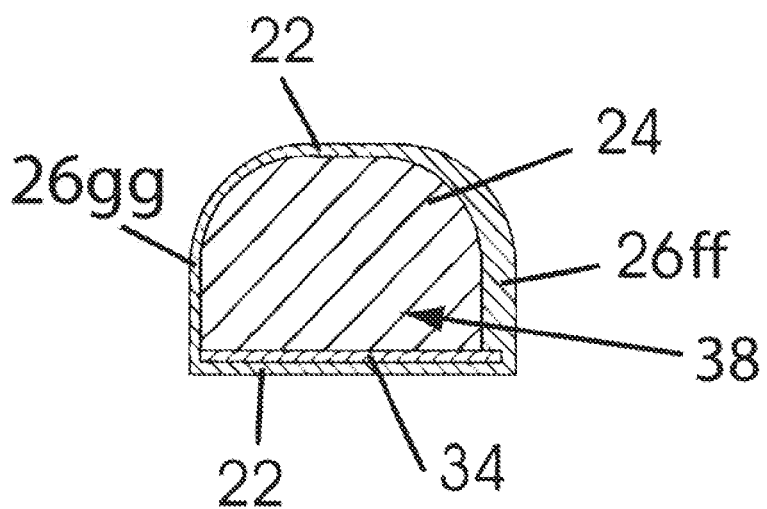
Figure 8C:
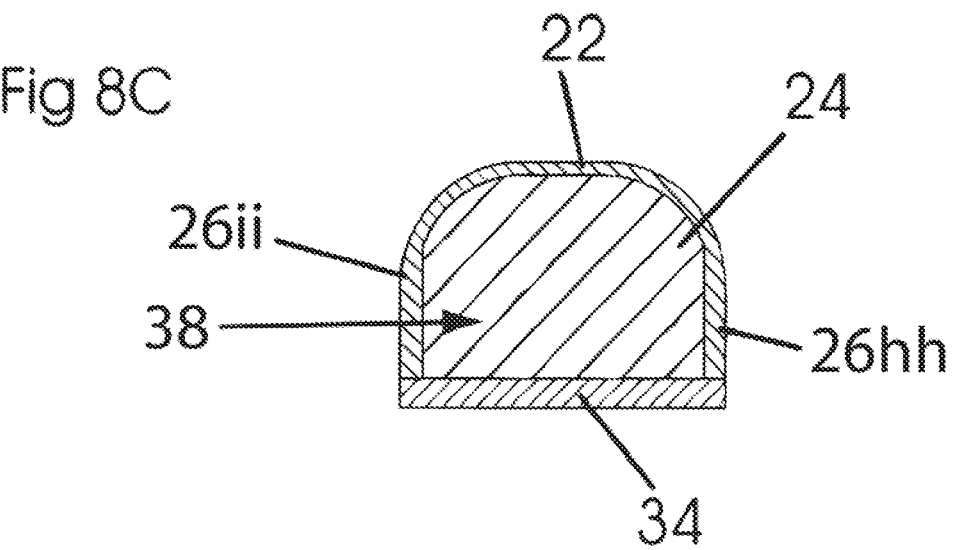

FIG. 8A-8C shows cross-sectional views of various configurations of single-arch mouthpiece 38, sheet 22, and filler 24. There are other possible configurations which are not shown, such as single-arch adaptations of configurations shown in FIGS. 1-7.

FIG. 8A shows a single-arch mouthpiece 38 wherein sheet 22 sealingly contains filler 24. Connector 34 connects facial wall 26*dd* to lingual wall 26*ee*. Separator 28 is shown lining the inner surface of sheet 22.

It is preferred that sheet 22 and contained filler 24 are removable from walls 26*dd* and 26*ee* and from connector 34. However, sheet 22 may be affixed to walls 26*dd* and 26*ee* and connector 34.

It is preferred that connector 34 is thin to permit flexing of walls 26*dd* and 26*ee*, thereby reducing interferences to seating the teeth into mouthpiece 38. However, connector 34 may be thicker and rigid, such as to facilitate forceful seating of the teeth. Further, connector 34 may be wedge-shaped, wherein connector 34 is thinner in the posterior portion of mouthpiece 38, and thicker in the anterior portion, such that the teeth of the opposing arch may forcefully occlude against connector 34 to facilitate forceful seating of the teeth into mouthpiece 38.

FIG. 8B shows a single-arch mouthpiece 38 wherein facial wall 26*ff* is comprised of thickened sheet 22. Connector 34 connects facial wall 26*ff* to lingual wall 26*gg*. Sheet 22 sealingly contains filler 24 and connector 34.

FIG. 8C shows a single-arch mouthpiece 38 wherein facial wall 26*hh* and lingual walls wall 26*ii* are comprised of thickened sheet 22. Connector 34 connects facial wall 26*hh* to lingual wall 26*ii*. Filler 24 is sealingly contained by sheet 22 and connector 34.

FIG. 9 is an enlarged perspective cutaway view showing a section of a sheet 22 having an indicating means, capsules 46. Capsules 46 contain an indicator, indicator 48. Capsules 46 are constructed to be rupturable under pressure from occlusion of teeth upon a sheet 22 which contains capsules 46, such as when a custom dental tray comprised of a sheet 22 is inserted between forcefully occluding dental arches. When capsules 46 are ruptured, indicator 48 is spilled from ruptured capsules 46. Some capsules 46 are shown entirely embedded within sheet 22, and some are shown partly embedded within sheet 22.

It is preferred that capsules 46 are graded according to various pressures required to cause rupture of selected capsules 46. For example, a first grade capsule 46 may rupture at a given occlusal pressure, called the rupture pressure. The rupture pressure of a second grade capsule 46 may be twice the rupture pressure of said first grade capsule 46. The indicator 48 contained in said first grade capsule 46 is distinguishable from indicator 48 contained in said second grade capsule 46. As such, graded capsules 46 may enable distinguishing degrees of bruxism severity.

It is preferred that a porous layer, absorbent 50, encloses the outer surface of capsules 46, such that spilled indicator 48 may be absorbed into absorbent 50, especially when capsules 46 are embedded in sheet 22, thereby enhancing the observability of indicator 48. Suitable materials for absorbent 50 include open-cell foam, fine hair-like projections set perpendicularly to the surface of capsule 46, and so on. However, capsules 46 may be embedded in sheet 22 without absorbent 50, or any other layer to enhance visibility of indicator 48. Further, capsules 46 may be located in a space, space 52, within sheet 22, or in a space 52 contained in an outer capsule, container 54, wherein said outer capsule encloses and defines space 52 within sheet 22. It is preferred that space 52 contains only air or gas. However, space 52 may be evacuated, or space 52 may contain materials, such as color enhancers, absorbent materials, and so on. It is preferred that container 54 is highly translucent, to enhance visibility of indicator 48.

It is preferred that capsules 46 are embedded within sheet 22. However, capsules 46 may be at least partly located on an external surface of sheet 22.

It is preferred that spilled indicator 48, in portions of sheet 22 which have been subjected to forceful occlusion, is distinguishable to an observer. It is further preferred that indicator 48 is distinguishable visually, such as when indicator 48 is a pigmented liquid or powder. However, indicator 48 may be comprised of a substance that is distinguishable under ultraviolet or infrared light, or may require use of an electronic detector.

It is preferred that indicator 48 is not comprised of a medicament. However, indicator 48 may be at least partly comprised of a medicament, such as a muscle relaxant for the treatment of severe myofacial pain dysfunction. It is preferred that capsules 46 which contain a medicament indicator 46 are primarily located at the surface of sheet 22, such that capsules 46 which are ruptured by occlusal force may release said medicament into the mouth. Routes of potential absorption of said medicament include: through the oral mucosa and into the bloodstream, through the oral mucosa and into the muscles of mastication, and through the gastro-intestinal tract.

It is preferred that sheet 22 is provided with a pressure indicating means, such as capsules 46. However, sheet 22 may be provided with no pressure indicating means, or sheet 22 may be provided with other pressure indicating means, such as conductive pressure-sensitive ink, other electronic pressure sensors, PTFE, and so on.

Where sheet 22 is fabricated with electronic pressure indicating means, such as pressure sensitive ink or electronic pressure sensors, then it is preferred that a memory device or electronic output connection is associated with sheet 22. As such, devices such as a bruxism recorder, bruxism alarm, or bruxism treatment modality, can receive data from sheet 22, whether said devices are located remotely, or are resident with sheet 22.

Figure 10:
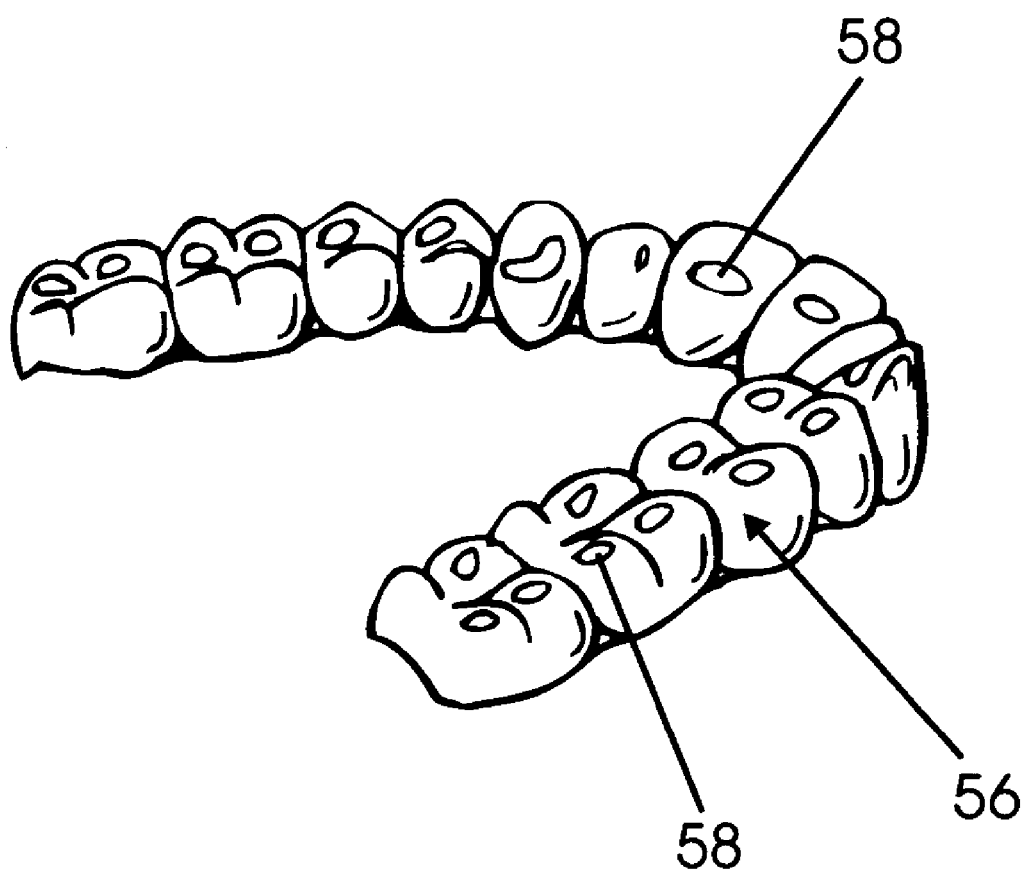
FIG. 10 shows a perspective view of a molded custom tray that has recorded occlusal contact pressures.

FIG. 10 shows a perspective view of a molded custom dental tray, tray 56, formed from a molded sheet 22. The tray 56 shown is comprised of a sheet 22 which contains capsules 46. Tray 56 has been subjected to forceful occlusal contact pressures, which have ruptured a portion of capsules 46 in multiple areas of occlusal contact. Where indicator 48 is spilled from ruptured capsules 46, distinguishable marks, records 58, are shown on sheet 22 in the immediate areas of occlusal contact.

From the description above, a number of advantages of my tray and process become evident:

(a) by persons unskilled in the art without the use of costly equipment (b) in fewer steps, and requiring shorter time, than other processes (c) for maxillary and mandibular arches simultaneously (d) which have low fluid leakage and substantial retention (e) which can indicate occlusal contact pressure (f) by persons unskilled in the art in order to retain attachments.

Another advantage is that accurately adapted custom dental trays can now be made by persons of the general public. In addition, they can be made rapidly and cost effectively in dental offices, or at home.

OPERATION—FIGS. 1-10

The invention provides a process for forming custom dental trays, especially occlusal indicator trays, comprising the steps of providing a mouthpiece comprised of moldable sheet 22 and contained moldable filler 24, forcefully pushing user's teeth into sheet 22 thereby molding sheet 22 to fit the shapes of the teeth, causing sheet 22 to become substantially non-moldable, removing said mouthpiece from user's teeth, trimming sheet 22 to form a custom tray.

It is preferred that sheet 22 is caused to be moldable by immersing in warm water, such as by immersing a low-melting thermoplastic sheet 22 into water warmed to a specified temperature within the approximate range of 40° to 85° C. As such, sheet 22 becomes moldable at a sufficiently low temperature to be tolerated in the mouth. However, sheet 22 may be made to be moldable by the user by other means, such as by exposure to chemicals, gasses, radiation, and so on, or sheet 22 may be moldable as provided from the manufacturer.

It is preferred that moldable sheet 22 is made to be non-moldable by cooling to approximately below 40° C. It is further preferred that intraoral cooling of sheet 22 is accelerated by various means, such as exposing sheet 22 to cool water, air, 1,1,1,2-tetrafluoroethane, ethyl chloride, and so on. However, sheet 22 can be made to be non-moldable by allowing sufficient time for the heat to be absorbed into the mouth, or by exposing to oxygen, saliva, light, cross-linking chemicals, gasses, radiation, and so on.

EXAMPLE 1

A first example of a process utilizing basic mouthpiece 20, in this case to form a medicament tray 56, begins with user heating water to 80° C. From a kit provided, user removes a mouthpiece 20 as shown in FIG. 3, a hook for holding mouthpiece 20 underwater, small scissors, and a syringe filled with a medicament.

User places said hook into a small hole in handle 32, and holds said hook to pull basic mouthpiece 20 down into the heated water, as basic mouthpiece 20 tends to float. Basic mouthpiece 20 is held under the heated water until sheet 22 becomes moldable. Basic mouthpiece 20 is removed from the heated water, and is inserted into user's mouth. User forcefully bites the upper and lower arches of teeth into basic mouthpiece 20 until the upper and lower portions of sheet 22 contact separator 28. Filler 24 provides sufficient resistance pressure to mold sheet 22 to fit the shapes of the teeth. Separator 28 inhibits adhesion of the upper portion of sheet 22 to the lower portion of sheet 22. Sheet 22 is allowed time to cool to body temperature, so as to become non-moldable. Basic mouthpiece 20 is removed from user's mouth. Sheet 22 is trimmed with scissors to form upper and lower trays 56.

User syringes a medicament, such as a tooth whitener, an antibacterial, a cariostatic, or such, onto the inner surfaces of trays 56, and trays 56 are seated onto the teeth for a specified time.

EXAMPLE 2

A second example of a process utilizing basic mouthpiece 20 as shown in FIG. 1, in this case to hold an attachment, begins with a dentist affixing an attachment, or template thereof, in a patient's mouth, such as by affixing a false tooth in a space left by a missing tooth in a patient's mouth. Said false tooth is affixed into said space in such a way that a small undercut remains under said false tooth, such that sheet 22 can later be molded into said undercut, and thereby retain said false tooth in basic mouthpiece 20, and later in tray 56. A user inserts basic mouthpiece 20 into a rigid dental stock tray. Said stock tray has a wedge-shaped occlusal pad on the surface which will face the opposing dental arch, thereby facilitating forceful occlusion of the teeth onto said stock tray. User heats water to 80° C. Basic mouthpiece 20 is held under the heated water by holding said stock tray handle until sheet 22 becomes moldable. Said stock tray containing basic mouthpiece 20 is inserted into patient's mouth. The patient forcefully bites against said stock tray such that the teeth are forcefully seated into basic mouthpiece 20, until sheet 22 contacts separator 28. Filler 24 provides sufficient resistance pressure to mold sheet 22 to fit the shapes of the teeth, including said attachment, the false tooth. Sheet 22 is allowed time to cool to become non-moldable. Said stock tray, containing basic mouthpiece 20 and said false tooth, is removed from the patient's mouth. Basic mouthpiece 20, retaining said false tooth, is removed from said stock tray. Sheet 22 is trimmed with scissors to form a tray 56. Tray 56, still retaining said false tooth, is placed into the patient's mouth as a rapid cosmetic tooth replacement.

Other suitable attachments for this example include occlusal pressure sensors, decorations, and so on.

EXAMPLE 3

An example of a process utilizing single-arch mouthpiece 38, in this case to form an economical occlusal indicator tray 56, begins with a dental office user selecting a single-arch mouthpiece 38 that is comprised of a sheet 22 containing capsules 46. Said single-arch mouthpiece 38 also has a source 42 comprising an elastic hand-squeezable bulb, as shown in FIG. 7. Said bulb is partly filled with water as a coolant.

User inserts single-arch mouthpiece 38 in a patient's mouth to check the fit. The curvatures of the patient's dental arches are found to be of slightly different than the curvature of single-arch mouthpiece 38 as provided from the manufacturer. User flexes single-arch mouthpiece 38 to a curvature that corresponds with the arches, and element 40 in single-arch mouthpiece 38 retains the new corresponding curvature.

Handle 32 is held while immersing single-arch mouthpiece 38 in the heated water until sheet 22 becomes moldable. Source 42 is not immersed in the heated water. Single-arch mouthpiece 38 is placed into a patient's mouth, and seated forcefully onto an arch of teeth, such that the teeth seat into moldable sheet 22. Filler 24 provides sufficient resistance pressure to mold sheet 22 to fit the shapes of the teeth. Source 42 bulb is hand-squeezed to introduce an atomized spray of cool water through valve 44, and into filler 24. Said water cools sheet 22, and thereby causes sheet 22 to become non-moldable. Single-arch mouthpiece 38 is removed from the patient's mouth. Sheet 22 is trimmed with scissors to form a tray 56.

Tray 56 is placed into the patient's mouth immediately prior to sleep, avoiding inadvertent pressures on sheet 22. The patient's teeth forcefully occlude during sleep, thereby applying pressure to rupture capsules 46 contained in portions of sheet 22. Moderate occlusal pressures rupture weaker capsules 46, which spills a first indicator 48, and thereby forms visible records 58, which corresponds to the color of first indicator 48, as shown in FIG. 10. Heavier occlusal pressures rupture stronger capsules 46, which spills a second indicator 48, and thereby forms visible records 58 which are colored according to relative combined amounts of first indicator 48 and second indicator 48.

The dentist examines tray 56, and notes changes in colorations, intensities, and patterns, of records 58 therein, to assess the degree of occlusal activity during the patient's sleep. Tray 56 is electronically scanned into the patient's records.

EXAMPLE 4

An example of a process utilizing double-arch mouthpiece 36, in this case to form a medicament tray 56, begins with user heating water to 80° C. From a kit provided, user removes a double-arch mouthpiece 36, as shown in FIG. 5, a source 42 which is comprised of a valved, pressurized can of 1,1,1-tetrafluoroethane coolant, connecting tubing for source 42, a small pair of scissors, and syringes filled with a medicament, such as a tooth whitener, an antibacterial, a cariostatic, or such.

Source 42 connecting tubing is connected to valve 44 on double-arch mouthpiece 36, but not to source 42. Handle 32 is inserted into a plastic microwave stand to orient handle 32 and double-arch mouthpiece 36 vertically, and double-arch mouthpiece 36 is placed into a microwave oven. Double-arch mouthpiece 36 is heated sufficiently such that water vapor in filler 24 causes sheet 22 to become moldable. The pressure of filler 24 is also somewhat increased.

Double-arch mouthpiece 36 is removed from the oven, and is inserted into user's mouth. User forcefully bites upper and lower arches of teeth into double-arch mouthpiece 36 until upper and lower portions of sheet 22 contact connector 34. The flexibility of connector 34 and walls 26s and 26t facilitate the occlusion of the opposing dental arches, while providing sufficient back pressure for filler 24 to facilitate molding sheet 22 to fit the shapes of the teeth.

Source 42 connecting tubing is connected to source 42. A valve on said pressurized can of source 42 is activated, thereby introducing coolant into filler 24 from source 42. Said coolant quickly cools sheet 22, and thereby causes sheet 22 to become non-moldable.

Double-arch mouthpiece 36 is removed from user's mouth. Upper and lower sheet 22 is trimmed with scissors to form upper and lower trays 56. Said medicament is placed on the inner surfaces of trays 56, and trays 56 are seated onto the teeth for a specified time.

By using the dental tray material of the invention, it is now possible, surprisingly, to form an accurately conformed dental tray intraorally, without requiring costly equipment.

The process offers the advantage that the dental practitioner can now produce accurately adapted dental trays in a short time, such as trays which can record occlusal pressure. The process offers a further advantage that unskilled persons can now produce accurately adapted dental trays, such as in their own homes.

SUMMARY, RAMIFICATIONS AND SCOPE

Accordingly, the reader will see that the dental tray material of this invention permits formation of accurately adapted custom dental trays to be formed intraorally in a short amount of time, and without the need for costly equipment. Furthermore, the dental tray material and process has the additional advantages in that it permits formation of accurate trays which can record occlusal pressures.

Although the description above contains many specificities, these should not be construed as limiting the scope of the invention and process, but as merely providing illustrations of some of the presently preferred embodiments of this invention.

As an example, by utilizing the occlusal indicator tray and process of this invention a dental practitioner may quickly form accurate trays 56. As a result, the practitioner may elect to use trays 56 to isolate and contain irritating in-office tooth-whitening gel. A scalloped tray 56 is coated inside with whitening gel, gingival dam resin is placed on the gingiva and left uncured, tray 56 is seated on the teeth such that the margins of tray 56 embed into said resin, said resin is cured to form a seal between the gingival and tray 56. Other gingival sealing materials may be substituted for said resin, such as non-curing materials, including sticky putty or denture adhesive.

Thus the scope of the invention should be determined by the appended claims and their legal equivalents, rather than by the examples given. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. A mouthpiece for forming dental custom trays comprising a moldable filler that provides resistance pressure against the forceful seating of teeth, and a custom tray sheet, wherein said filler is entirely enclosed and sealingly contained at least by said sheet when said sheet is molded by forceful imprinting with teeth, wherein said mouthpiece has a facial side, an occlusal side, and a lingual side, and a supporting wall that is absent from at least the occlusal side, wherein said supporting wall is more rigid than said sheet, wherein said sheet is comprised of a low-melting thermoplastic, and said filler is comprised a material that remains moldable after said sheet has been molded to fit the shapes of the teeth.

2. The mouthpiece of claim 1, wherein a maxillary and a mandibular custom tray are formed simultaneously.

* * * * *